United States Patent
Roby et al.

(10) Patent No.: US 6,277,927 B1
(45) Date of Patent: Aug. 21, 2001

(54) ABSORBABLE BLOCK COPOLYMERS AND SURGICAL ARTICLES FABRICATED THEREFROM

(75) Inventors: Mark S. Roby, Killingworth, CT (US); Ying Jiang, Raleigh, NC (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/198,035

(22) Filed: Nov. 23, 1998

Related U.S. Application Data

(60) Provisional application No. 60/066,560, filed on Nov. 26, 1997.

(51) Int. Cl.⁷ .......................... C08G 63/08; A61L 17/12
(52) U.S. Cl. .......................... 525/411; 525/413; 525/415; 528/354; 606/230
(58) Field of Search .................. 525/411, 413, 525/415; 528/354; 606/230

(56) References Cited

U.S. PATENT DOCUMENTS

| | | | |
|---|---|---|---|
| 2,668,162 | 2/1954 | Lowe | 260/78.3 |
| 2,683,136 | 7/1954 | Higgins | 260/78.3 |
| 2,703,316 | 3/1955 | Schneider | 260/78.3 |
| 2,758,987 | 8/1956 | Salzberg | 260/78.3 |
| 3,225,766 | 12/1965 | Baptist et al. | 128/335.5 |
| 3,268,486 | 8/1966 | Klootwijk | 260/78.3 |
| 3,268,487 | 8/1966 | Klootwijk | 260/78.3 |
| 3,297,033 | 1/1967 | Schmitt | 128/335.5 |
| 3,422,181 | 1/1969 | Chirgwin, Jr. | 264/345 |
| 3,442,871 | 5/1969 | Schmitt et al. | 260/78.3 |
| 3,463,158 | 8/1969 | Schmitt et al. | 128/334 |
| 3,468,853 | 9/1969 | Schmitt et al. | 260/78.3 |
| 3,531,519 | 9/1970 | Parkin et al. | 260/524 |
| 3,565,869 | 2/1971 | DeProspero | 260/78.3 |
| 3,597,449 | 8/1971 | DeProspero et al. | 260/340.2 |
| 3,620,218 | 11/1971 | Schmitt et al. | 128/334 R |
| 3,626,948 | 12/1971 | Glick et al. | 128/335.5 |
| 3,636,956 | 1/1972 | Schneider | 128/335.5 |
| 3,733,919 | 5/1973 | Rupp, II | 74/242.16 |
| 3,736,646 | 6/1973 | Schmitt et al. | 29/458 |
| 3,772,420 | 11/1973 | Glick et al. | 264/102 |
| 3,781,349 | 12/1973 | Ramsey et al. | 260/535 P |
| 3,784,585 | 1/1974 | Schmitt et al. | 260/861 |
| 3,792,010 | 2/1974 | Wasserman et al. | 260/32.2 R |
| 3,797,499 | 3/1974 | Schneider | 128/334 R |
| 3,839,297 | 10/1974 | Wasserman et al. | 260/78.3 R |
| 3,846,382 | 11/1974 | Ramsey et al. | 260/78.3 R |
| 3,867,190 | 2/1975 | Schmitt et al. | 117/138.8 A |
| 3,878,284 | 4/1975 | Schmitt et al. | 264/184 |
| 3,902,497 | 9/1975 | Casey | 128/296 |
| 3,937,223 | 2/1976 | Roth | 128/325 |
| 3,982,543 | 9/1976 | Schmitt et al. | 128/335.5 |
| 3,987,937 | 10/1976 | Coucher | 222/193 |
| 4,033,938 | 7/1977 | Augurt et al. | 260/78.3 R |
| 4,045,418 | 8/1977 | Sinclair | 260/78.3 R |
| 4,052,988 | 10/1977 | Doddi et al. | 128/335.5 |
| 4,057,537 | 11/1977 | Sinclair | 260/78.3 R |
| 4,060,089 | 11/1977 | Noiles | 128/325 |
| 4,137,921 | 2/1979 | Okuzumi et al. | 128/335.5 |
| 4,157,437 | 6/1979 | Okuzumi et al. | 528/354 |
| 4,243,775 | 1/1981 | Rosensaft et al. | 525/415 |
| 4,246,904 | 1/1981 | Kaplan | 128/335.5 |
| 4,273,920 | 6/1981 | Nevin | 528/361 |
| 4,275,813 | 6/1981 | Noiles | 206/339 |
| 4,279,249 | 7/1981 | Vert et al. | 128/92 D |
| 4,300,565 | 11/1981 | Rosensaft et al. | 128/335.5 |
| 4,429,080 | 1/1984 | Casey et al. | 525/415 |
| 4,526,938 | 7/1985 | Churchill et al. | 525/415 |
| 5,133,739 | 7/1992 | Bezwada et al. | 606/230 |
| 5,252,701 | 10/1993 | Jarrett et al. | 528/354 |
| 5,403,347 | 4/1995 | Roby et al. | 606/230 |
| 5,431,679 | 7/1995 | Bennett et al. | 606/230 |
| 5,502,159 | 3/1996 | Liu et al. | 528/354 |
| 5,522,841 | 6/1996 | Roby et al. | 606/230 |
| 5,554,170 | 9/1996 | Roby et al. | 606/230 |

FOREIGN PATENT DOCUMENTS

| | | |
|---|---|---|
| 779291 | 7/1957 | (GB) . |
| 1332505 | 10/1973 | (GB) . |
| 1414600 | 11/1975 | (GB) . |
| 2102827 | 2/1983 | (GB) . |

Primary Examiner—David J. Buttner

(57) ABSTRACT

Block copolymers wherein the first block contains from about 20 to about 80 mole percent of repeating units derived from lactide randomly combined with from about 20 to 80 mole percent of repeating units derived from glycolide and the second block contains repeating units derived from lactide and repeating units derived from other bioabsorbable monomeric units, such as glycolide, the second block containing a higher proportion of repeating units derived from lactide than the first block, with units derived from lactide constituting from about 40 to about 90 mole percent of the entire block copolymer are useful in forming surgical articles, including sutures.

11 Claims, 2 Drawing Sheets

ABSORBABLE BLOCK COPOLYMERS AND SURGICAL ARTICLES FABRICATED THEREFROM

This Application claims the benefit of U.S. Provisional Application No. 60/066,560 filed Nov. 26, 1997.

TECHNICAL FIELD

Absorbable block copolymers having one of the blocks made from randomly polymerized glycolide and lactide and another block made substantially entirely from lactide are described. Processes for making the copolymers and surgical articles made totally or in part from such copolymers, including sutures, are also described.

BACKGROUND

Bioabsorbable surgical devices made from copolymers derived from glycolide and lactide are known in the art. Such bioabsorbable surgical devices include surgical sutures.

A desirable characteristic of a bioabsorbable suture is its ability to exhibit and maintain desired tensile properties for a predetermined time period followed by rapid absorption of the suture mass (hereinafter "mass loss".)

Absorbable multifilament sutures such as DEXON sutures (made from glycolide homopolymer and commercially available from Davis & Geck, Danbury, Conn.), VICRYL sutures (made from a copolymer of glycolide and lactide and commercially available from Ethicon, Inc., Sommerville, N.J.), and POLYSORB sutures (also made from a copolymer of glycolide and lactide and commercially available from United States Surgical Corporation, Norwalk, Conn.) are known in the industry as short term absorbable sutures. The classification short term absorbable sutures generally refers to surgical sutures which retain at least about 20 percent of their original strength at three weeks after implantation, with the suture mass being essentially absorbed in the body within about 60 to 90 days post implantation.

Early attempts to increase in vivo strength retention have resulted in monofilament sutures, which are generally classified as long term absorbable sutures capable of retaining at least about 20 percent of their original strength for six or. more weeks after implantation, with the suture mass being essentially absorbed in the body within about 180 days post implantation. For example, PDS II sutures (commercially available from Ethicon, Inc., Sommerville, N.J.), are synthetic absorbable monofilament sutures that reportedly retain at least about 20 to 30 percent of its original strength six weeks after implantation. However, PDS II reportedly exhibits minimal mass loss until 90 days after implantation with the suture mass being essentially absorbed in the body about 180 days after implantation. MAXON suture (commercially available from Davis & Geck, Danbury, Conn.) is another absorbable synthetic monofilament that reportedly generally fits this absorption profile.

Later attempts to provide an acceptable absorbable monofilament sutures resulted in MONOCRYL sutures, a suture available from Ethicon, Inc.

Most recently, United States Surgical Corporation has introduced BIOSYN monofilament sutures which exhibit good flexibility, handling characteristics, knot strength and absorption characteristics similar to those of presently available short term absorbable multifilament sutures.

It would be advantageous to provide a bioabsorbable synthetic multifilament surgical suture which exhibits and maintains tensile properties and handling characteristics comparable to commercially available long term absorbable monofilament sutures, without substantially increasing the time at which the suture mass is absorbed in the body.

SUMMARY

It has now surprisingly been found that absorbable surgical articles formed from a block copolymer having one of the blocks made from a random copolymer of glycolide and lactide and another block made from a predominant amount of lactide combined with glycolide exhibit increased in vivo strength retention without exhibiting any substantial decrease in the rate of bioabsorption as measured by mass loss. Preferably, the block copolymers used in forming surgical articles include one block having between about 20 and about 80 mole percent of lactic acid ester units and between about 80 and 20 mole percent of glycolic acid ester units, and lactic acid ester units constitute from about 40 to about 90 mole percent of the overall block copolymers.

The copolymers are prepared by first copolymerizing glycolide and lactide to form a random prepolymer. Lactide is then added to the reaction vessel and combines with the random prepolymer and any residual unreacted monomer to produce a block copolymer.

In particularly useful embodiments, the block copolymers can be spun into fibers. The fibers can be advantageously fabricated into braided multifilament sutures.

DESCRIPTION OF THE PREFERRED EMBODIMENTS

Figure 1:
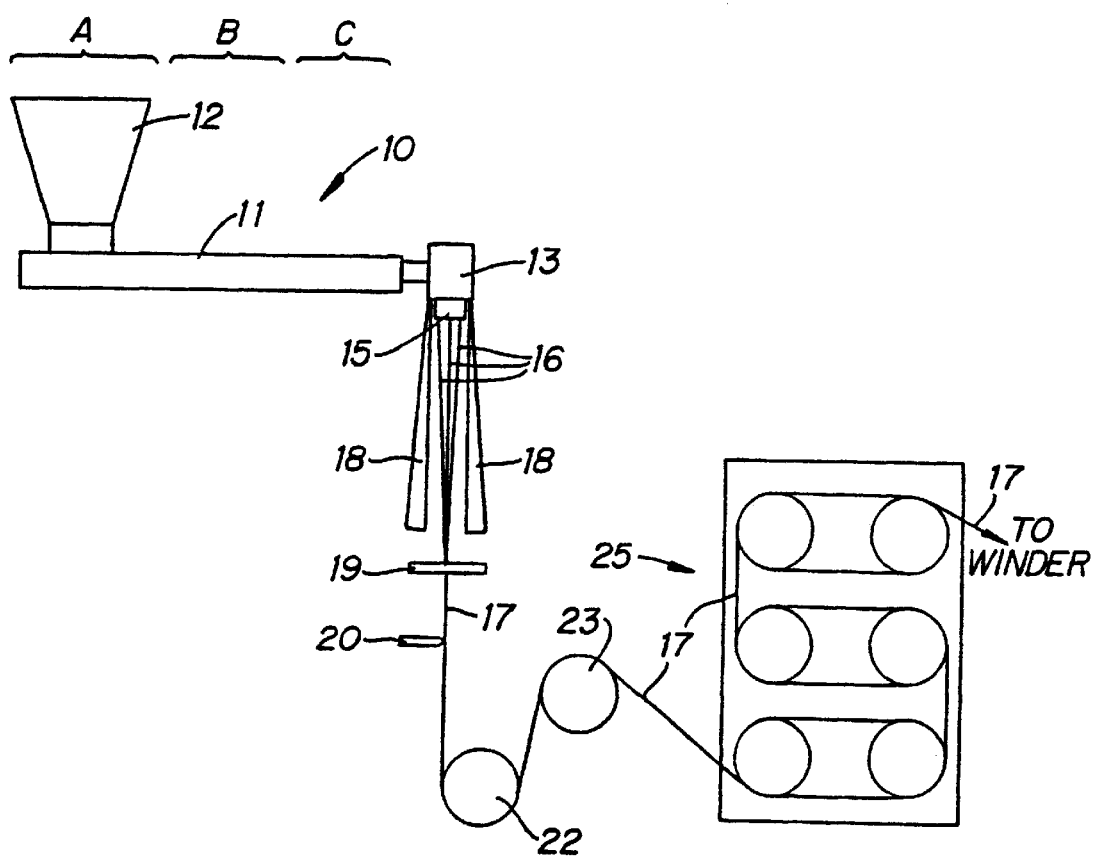
FIG. 1 is a schematic illustration of an apparatus which is suitable for manufacturing multifilament yarns in accordance with this disclosure.

It has been found that a block copolymer having two specific types of blocks, an "A" block having a proportion of glycolic acid ester linkages randomly combined with lactic acid ester linkages and a "B" block including lactic acid ester linkages can advantageously be combined to form a block copolymer useful in forming surgical elements.

The block copolymers include an A block formed from a copolymer which has repeating units derived from glycolide randomly combined with repeating units derived from lactide. Repeating units derived from lactide comprise between about 20 and about 80 mole percent of the first block and preferably about 40 to about 60 mole percent of the first block. Most preferably, lactide comprises about 45 to about 55 mole percent of the first block. Copolymers of glycolide and lactide having an inherent viscosity of from about 1.2 to about 1.7 dl/g measured at 30° C. and at a concentration of 0.25 g/dl in chloroform or HFIP may generally be used as the first block.

The B block of the copolymer comprises lactide. Preferably lactide comprises at least about 60 mole percent, and more preferably greater than about 80 mole percent of the B block. Most preferably, the B block comprises about 90 mole percent lactide. It should be understood that the B block may also contain amounts of other absorbable copolymers, such as glycolide.

The block copolymers can be made using any technique known to those skilled in the art. Thus, for example, each block can be individually formed as a prepolymer and then the prepolymers can be reacted to form the desired block copolymer. In a particularly useful embodiment, the copolymer is prepared by first preparing a pre-polymer made from glycolide and lactide. The prepolymer can be prepared using conventional techniques. For example, monomers can be dried, mixed in a reaction vessel with an initiator (either a single or multi-functional initiator) and a suitable polymerization catalyst and heated at temperatures from about 160° C. to about 200° C. for a period of time ranging from about 5 hours to about 10 hours. Then, lactide is added directly to the reactor and reacts with the prepolymer and any residual monomer to thereby form the block copolymer. Preferably, lactide is added and polymerized at temperatures from about 160° C. to about 200° C. for a time varying between about 5 and 10 hours from the time addition of the lactide is complete. It should be understood that a combination of glycolide and lactide can be added to form the second block provided the overall composition of the block copolymer is as described herein.

In forming the block copolymers, the A block may be present in an amount from about 40 to about 60 percent by weight based on the weight of the final block copolymer. The B block may be present in an amount from about 40 to about 60 weight percent based on the weight of the final block copolymer. Preferably, the A block comprises between about 40 and about 60 weight percent of the block copolymer. In a particularly useful embodiment, the A block comprises about 50 weight percent and the B block comprises about 50 weight percent of the final block copolymer. The copolymers can have a molecular weight such that their inherent viscosity is from about 1.2 to about 2 dl/g, and preferably from about 1.3 to about 1.6 dl/g measured at 30° C. at a concentration of 0.25 g/dl in hexafluoroisopropanol (HFIP).

The block copolymers may have repeating block units such as AB, BAB, and any combination thereof, such as e.g., BABAB, with AB being preferred.

The block copolymers can be formed into surgical articles using any known technique, such as, for example, extrusion, molding and/or solvent casting. The copolymers can be used alone, blended with other absorbable compositions, or in combination with non-absorbable components. A wide variety of surgical articles can be manufactured from the copolymers described herein. These include but are not limited to clips and other fasteners, staples, sutures, pins, screws, prosthetic devices, wound dressings, drug delivery devices, anastomosis rings, and other implantable devices. Fibers made from the present copolymers can be knitted, woven or made into non-woven materials with other fibers, either absorbable or nonabsorbable to form fabrics, such as meshes and felts. Compositions including these block copolymers can also be used as an absorbable coating for surgical devices. Preferably, however, the copolymers are spun into fibers to be used in making sutures.

FIG. 1 schematically illustrates a filament manufacturing operation suitable for use with the polymers described herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resin to be spun into filaments are introduced to the extruder through hopper 12. Any of the polymeric resins which are useful for the formation of fibers can be used herein.

Motor-driven metering pump 13 delivers extruded resin at a constant rate through spinneret 15 possessing one or more orifices of desired diameter to provide a plurality of molten filaments 16. While spinneret 15 is shown schematically in FIG. 1 as extruding three filaments, it should be understood that the spinneret may extrude anywhere from 1 to 200 or more filaments simultaneously.

The filaments 16 travel downward and are gathered together by guide 19 to produce a yarn 17. The distance the filaments 16 travel after emerging from spinneret 15 to the point where they contact guide 19, i.e., the air gap, can vary and can advantageously be from about 0.5 m to about 10 m and preferably from about 1 m to about 2 m. A chimney 18, or shield, can be provided to isolate filaments 16 from contact by air currents which might otherwise affect the cooling or movement of the filaments in some unpredictable manner. In general, the temperature of zones A, B and C of the barrel 11 will vary depending on a number of factors such as the size of the powder or pellets and the rate of feed.

Once filaments 16 are gathered together by guide 19 to produce yarn 17, a spin finish can be applied to yarn 17, if desired, using any known technique.

As shown in FIG. 1, the yarn may be wrapped around a lub godet 22 and one or more additional godets, for example, godet 23, to take up and adjust the tension on the yarn. The yarn 17 may then be passed to a heated draw frame 25. Draw frame 25 may be of any configuration. As shown in FIG. 1, draw frame 25 can include three pairs of godets which can be used to stretch the yarn or to allow relaxation and perhaps shrinkage of yarn 17. The speed at which the godets rotate and the temperature at which the draw frame is maintained will determine the amount of stretching and/or relaxation which occurs. Setting the various speeds and temperatures to achieve a desired result is within the purview of those skilled in the art.

Table I provides suitable ranges of values for spinning and stretching parameters useful in producing yarns from the present copolymers.

TABLE I

MELT SPINNING APPARATUS AND OPERATING CONDITIONS

| Apparatus Component,Operating Parameter | |
|---|---|
| Extruder barrel temp., zone A, ° C. | 185–195 |
| Extruder barrel temp., zone B, ° C. | 185–195 |
| Extruder barrel temp., zone C, ° C. | 185–195 |
| Extruder barrel pressure, psi | 700–2500 |
| Extruder barrel melt temp., ° C. | 200–260 |
| Pump size, cc per rev. | .16–.584 |
| Pump rpm | 10–50 for size .16 pump |
| | 3–11 size .584 pump |
| Pump temp., ° C. | 185–195 |
| Pump pressure, psi | 500–2500 |
| Pump melt temp., ° C. | 190 |
| Block temp., ° C. | 190 |
| Clamp temp., ° C. | 190 |
| Adapter temp., ° C. | 190 |
| Candle filter, screen, microns | 10–60 |
| No. of spinneret | 5–200 |
| Diameter of spinneret orifices, .001 in | 5–30 |
| Spinneret temp., ° C. | 185–195 |
| Spinneret pressure, psi | 500–2500 |
| Spinneret melt temp., ° C. | 185–195 |
| cc/hr output, per spinneret | 5–20 |
| First pair of godets, ° C. | 50–80 |
| First pair of godets, mpm | 80–275 |
| Second pair of godets, ° C. | 60–120 |
| Second pair of godets, mpm | 675–1610 |
| Draw (stretch) ratio | 2–6 |
| Third pair of godets, ° C. | ambient |
| Third pair of godets, mpm | 750–1400 |
| Shrinkage (relaxation), percent | 5–10 |

After drawing, the yarn may be sent to a winder where it can be placed onto spools for storage while awaiting further treatment and/or braiding. Any spin finish can be removed from the yarn by washing.

Sutures made from the copolymers described herein can be prepared by methods known in the art Braid constructions and methods suitable for making multifilament suture using the copolymers described herein include those disclosed in U.S. Pat. Nos. 5,059,213 and 5,019,093. The characteristics of the braided suture prepared in accordance with this disclosure, apart from the material of its construction, may include:

(1) overall suture denier;

(2) the pattern of the interlocking yarns expressed as the pick count, which is to say, the number of crossovers of individual sheath yarns per linear inch of suture;

(3) the number of sheath yarns comprising the braid;

(4) the denier of the individual filaments comprising each sheath yarn; and, (5) the denier of the core, where present.

(1) Overall Denier of the Suture

The overall denier of the braided suture can vary from about 25 to about 4300. Within this range, the ranges of overall denier for particular sutures are: from about 25 to about 80 denier; from above about 80 to about 150 denier; from above about 150 to about 300 denier; from above about 300 to about 600 denier; from above about 600 to about 950 denier; from above about 950 to about 1500 denier; from above about 1500 to about 2300 denier; and, from above about 2300 to about 4300 denier.

(2) Pattern of the Interlocking Sheath Yarns (Pick Count)

For a suture of any range of overall denier, pick count can vary from about 25 to about 100 crossovers/inch with about 40–85 crossovers/inch being preferred. For sutures constructed within any range of overall denier, as larger numbers of sheath yarns are employed, the pick-count for acceptable sutures will also increase within the above ranges.

For a suture of a particular range of denier and number of sheath yarns, pick count is advantageously established to achieve a balance in the properties desired. In general, with increasing pick count, surface roughness of the suture tends to increase and with decreasing pick count, the ability of the external braided sheath to contain the core (if present) tends to decrease even reaching the point where the braid may become so loose as to result in the core protruding therethrough.

(3) The Number of Sheath Yarns

The number of sheath yarns bears some relation to overall suture denier, the number generally increasing with the weight of the suture. Thus, across the range of suture weight (denier) indicated above, the braided suture of this invention can be constructed with from about 3 up to as many as about 36 individual sheath yarns constructed from individual filaments having the deniers discussed below.

Table II below sets forth broad and preferred ranges for the numbers of sheath yarns which are suitable for the construction of braided sutures of various ranges of overall denier. The pick counts of the sutures vary from about 50 to about 100 crossovers/inch and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 0.8 to about 1.6, for the preferred range of number of sheath yarns.

TABLE II

Sheath Yarns Related to Suture Denier

| Overall Suture Denier | Suture Size | Number of Sheath Yarns (Broad Range) | Number of Sheath Yarns (Preferred Range) |
|---|---|---|---|
| 25 to about 80 | 7/0, 8/0 | 3–12 | 3–8 |
| greater than about 80 to about 150 | 6/0 | 3–12 | 3–8 |
| greater than about 150 to about 300 | 5/0 | 4–16 | 6–14 |
| greater than about 300 to about 600 | 4/0 | 4–16 | 6–14 |
| greater than about 600 to about 950 | 3/0 | 4–16 | 6–14 |
| greater than about 950 to about 1500 | 2/0 | 6–24 | 12–20 |
| greater than about 1500 to about 2300 | 0 | 6–24 | 12–20 |
| greater than about 2300 to about 4300 | 1, 2 | 6–24 | 12–20 |

It is generally preferred that they be air entangled so as to minimize snagging during braid construction. Alternatively, the sheath yarns can be provided with a twist in lieu of being air entangled.

(4) Individual Filament Denier

The individual filaments comprising each sheath yarn can vary in size from about 0.2 to about 6.0 denier, preferably from about 0.8 to about 3.0 denier and more preferably from about 1.0 to about 1.8 denier. The number of such filaments present in a particular sheath yarn will depend on the overall denier of the suture as well as the number of sheath yarns utilized in the construction of the suture. Table III sets forth some typical numbers of filaments per sheath yarn for both the broad and preferred ranges of filament denier:

TABLE III

Number of Filaments per Sheath Yarn

| approximate minimum | approximate maximum | Filament Denier |
|---|---|---|
| 45 | 450 | 0.2 |
| 15 | 150 | 0.5 |
| 5 | 50 | 1.5 |
| 3 | 40 | 1.8 |
| 1 | 15 | 6.0 |

((5) Core Optional)

For all but the lowest range of overall denier, the braided suture herein can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier denier to possess a core.

Table IV below provides some typical core deniers for sutures of various deniers.

TABLE IV

Core Denier Related to Suture Denier

| Overall Suture Denier | Suture Size | Denier of Optional Core (Broad Range) | Denier of Optional Core (Preferred Range) |
|---|---|---|---|
| from about 25 to about 80 | 8/0, 7/0 | none | none |
| greater than about 80 to about 150 | 6/0 | 0–80 | none |
| greater than about 150 to about 300 | 5/0 | 0–100 | none |
| greater than about 300 to about 600 | 4/0 | 0–125 | none |
| greater than about 600 to about 950 | 3/0 | 0–300 | 30–90 |
| greater than about 950 to about 1500 | 2/0 | 0–700 | 150–250 |
| greater than about 1500 to about 2300 | 0 | 0–1200 | 200–300 |
| greater than about 2300 to about 4300 | 1, 2 | 0–2400 | 250–650 |

Figure 2:
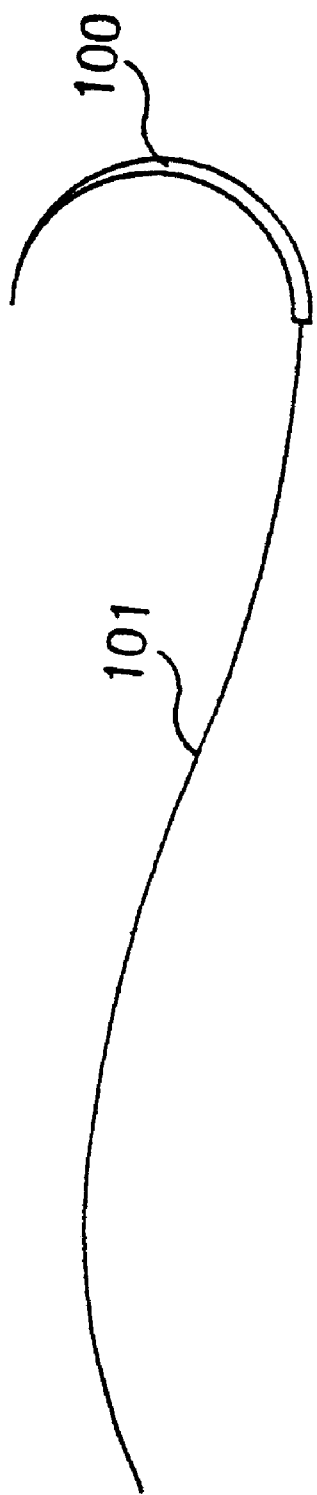
FIG. 2 is a perspective view of a suture made using the copolymers described herein attached to a needle.

A suture 101 may be attached to a surgical needle 100 as shown in FIG. 2 by methods well known in the art. Wounds may be sutured by passing the needled suture through tissue to create wound closure. The needle preferably is then removed from the suture and the suture tied.

It is further contemplated that one or more clinically useful substances can be incorporated into compositions containing, or used in conjunction with the copolymers described herein. Examples of such clinically useful substances include, for example, those which accelerate or beneficially modify the healing process when applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It may be desirable to dye the sutures made in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, the sutures are dyed by adding up to about a few percent and preferably about 0.2% dye, such as D&C Violet No. 2 to the resin prior to extrusion.

In order that those skilled in the art may be better able to practice the compositions and methods described herein, the following example is given as an illustration of the preparation of block copolymers as well as of the preparation and superior characteristics of sutures made from the copolymers. It should be noted that the invention is not limited to the specific details embodied in the examples and further that all ratios or parts recited are by weight, unless otherwise indicated.

EXAMPLE

Lactide (1500 grams) and glycolide (1500 grams) are added to a reactor along with 0.45 grams of stannous octoate and 3.6 grams of dodecanol. The mixture is dried for about six hours with agitation under flow of nitrogen. The reactor temperature is then set at 170° C., and polymerization conducted with stirring under a nitrogen atmosphere for about 5 hours. The glycolide/lactide random copolymer is then sampled.

A mixture of 2700 grams of lactide and 300 grams of glycolide is added to the reactor and then heated at 165° C. The polymerization is continued for about 10 hours. The copolymer is then extruded, pelletized and heated under vacuum to remove residual water, residual solvent and/or unreacted monomer. The resulting block copolymer contains about 80 mole percent lactide and about 20 mole percent glycolide.

Yarn containing 23 filaments having a denier in the range 34.9 to 38.6 is produced by spinning the copolymer. The filaments were dyed with about 0.2% D&C Violet No. 2. The spinning conditions employed to produce such filaments were as follows:

TABLE V

CONDITIONS OF MANUFACTURING MULTIFILAMENT SUTURES FROM THE BLOCK COPOLYMERS OF EXAMPLE

| Extrusion Conditions | |
|---|---|
| pump, rpm | 36.76 |
| barrel temp., ° C., zone A | 185 |
| barrel temp., ° C., zone B | 185 |
| barrel temp., ° C., zone C | 190 |
| mixer clamp temp., ° C. | 190 |
| pump temp., ° C. | 190 |
| block temp., ° C. | 190 |
| spinneret temp., ° C. | 185 |
| collar temp., ° C. | 200 |
| spinneret melt temp., ° C. | 190 |
| barrel pressure, psi | 930 |
| pump pressure, psi | 750 |
| spinneret pressure, psi | 1550 |
| pump size, cc per revolution | .16 |
| lube pump, rpm | 4.1 |
| Drawing (Orienting) Operation Example | |
| godet 1 temp., ° C. | 60 |
| first godet, mpm | 195 |
| second godet, mpm | 1120 |
| Godet 2 temp., ° C. | 85 |
| third godet, mpm | 1100 |
| draw ratio | 5.64 |
| Post Treatment/Annealing Operation Example | |
| oven temp., ° C. | 100 |

Modifications and variations of the compositions and processes disclosed herein are possible in light of the above teachings. It is therefore to be understood that changes may be made in particular embodiments described which are within the full intended scope of the invention as defined by the claims.

What is claimed is:

1. A block copolymer comprising:
   (a) a first block containing from about 20 to about 80 mole percent of repeating unites derived from lactide randomly combined with from about 20 to 80 mole percent of repeating units derived from glycolide; and
   (b) a second block containing of repeating units derived from lactide and repeating unites derived from glycolide, the second block containing about 60 to 100 lactide, the second block having a higher proportion of repeating units derived from lactide than the first block,
   the units derived from lactide constituting from about 58 to about 90 mole percent of the entire block copolymer.

2. A block copolymer as in claim 1 wherein the the units derived from lactide constitutes about 80 mole percent of the block copolymer.

3. A block copolymer as in claim 1 wherein the first block constitutes from about 30 to about 60 percent by weight of the entire copolymer.

4. A block copolymer as in claim 1 wherein the second block contains from about 60 to 100 mole percent lactide.

5. A block copolymer as in claim 1 wherein the second block contains about 90 mole percent lactide.

6. A block copolymer as in claim 1 wherein the block copolymer is a triblock copolymer.

7. A fiber made from the copolymer of claim 1.

8. A suture comprising a sterile fiber made from block copolymer having
   (a) a first block containing from about 20 to about 80 mole percent of repeating units derived from lactide randomly combined with from about 20 to 80 mole percent of repeating units derived from glycolide; and
   (b) a second block containing of repeating units derived from lactide and repeating units derived from glycolide, the second block containing about 60 to 100 lactide, the second block having a higher proportion of repeating units derived from lactide than the first block,
   units derived from lactide constituting from about 58 to about 90 mole percent of the entire block copolymer.

9. A suture as in claim 8, wherein the units derived from lactide constitute about 80 mole percent of the block copolymer.

10. A suture as in claim 8 wherein the first block of the copolymer constitutes from about 10 to about 60 percent by weight of the entire copolymer.

11. A suture as in claim 8 wherein the block copolymer is a triblock copolymer.

* * * * *